(12) United States Patent
Uang et al.

(10) Patent No.: US 8,309,715 B2
(45) Date of Patent: Nov. 13, 2012

(54) CAMPHOR-DERIVED β-AMINO ALCOHOL COMPOUNDS, METHOD FOR MANUFACTURING THE SAME AND ASYMMETRIC ADDITION OF ORGANOZINC TO ALDEHYDES USING THE SAME

(75) Inventors: Biing-Jiun Uang, Hsinchu (TW); Chi-Rui Wu, Hsinchu (TW); Hsyueh-Liang Wu, Hsinchu (TW); Ping-Yu Wu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 55 days.

(21) Appl. No.: 12/818,738

(22) Filed: Jun. 18, 2010

(65) Prior Publication Data

US 2011/0313159 A1 Dec. 22, 2011

(51) Int. Cl.
*C07D 265/30* (2006.01)
*C07D 211/06* (2006.01)
*C07D 207/04* (2006.01)
*C07C 29/14* (2006.01)

(52) U.S. Cl. ......... 544/173; 548/579; 546/206; 568/700
(58) Field of Classification Search .................. None
See application file for complete search history.

(56) References Cited

OTHER PUBLICATIONS

Wu et al., Tetrahedron: Asymmetry (2009), 20(13), p. 1556-1560.*
Martinez et al., Tetrahedron: Asymmetry, (2002), vol. 13, p. 1457-1460.*
Zhi-Long Wu, Hsyueh-Liang Wu, Ping-Yu Wu, and Biing-Jiun Uang; Asymmetric Addition of Diethylzinc to Aldehydes Catalyzed by a Camphor-Derived β-Amino Alcohol; *Tetrahedron: Asymmetry*; Jul. 14, 2009; p. 1556-p. 1560.

* cited by examiner

*Primary Examiner* — Yong Chu
(74) *Attorney, Agent, or Firm* — Muncy, Geissler, Olds & Lowe, PLLC

(57) ABSTRACT

A novel camphor-derived β-amino alcohol compound is disclosed. The novel camphor-derived β-amino alcohol compound can be used in asymmetric addition of organozinc to aromatic and aliphatic aldehydes, including linear aliphatic ones, thus generating corresponding secondary alcohols in high yields and enantiomeric excess.

9 Claims, No Drawings

CAMPHOR-DERIVED β-AMINO ALCOHOL COMPOUNDS, METHOD FOR MANUFACTURING THE SAME AND ASYMMETRIC ADDITION OF ORGANOZINC TO ALDEHYDES USING THE SAME

BACKGROUND OF THE INVENTION

1. Field of the Invention

The present invention relates to a camphor-derived β-amino alcohol compound, a method for manufacturing the same and asymmetric addition of organozinc to aldehydes using the same and, more particularly, to a easily prepared camphor-derived β-amino alcohol compound, a method for manufacturing the same and asymmetric addition of organozinc to aldehydes using the same.

2. Description of Related Art

Optically active alcohols play an important role in the synthesis of natural products, biologically active components, such as Orphenadrine, Neobenodine, Carbinoxamine, Efavirenz Fostriencin and Camptothecin. In particular, it has become increasingly clear that enantiomerically pure drugs have distinct biological activities, and thereby optically active alcohols may be critical intermediates for synthesis of new drugs.

The production of enantiomerically pure material has historically been achieved in one of two ways: the use of enantiomerically pure starting materials derived from natural sources (so-called chiral pool); and the resolution of racemic mixtures by classical techniques. However, the chiral pool is limited to compounds found in nature, so only certain structures and configurations are readily available. Regarding resolution of racemates, it may be inconvenient and time-consuming since the use of resolving agents is required.

Accordingly, asymmetric synthetic methods utilizing highly efficient chiral catalysts and auxiliaries have attracted the attention of synthetic organic chemists. Among the methods available for the synthesis of chiral alcohols, the enantioselective addition of organozincs to carbonyl compounds in the presence of chiral substances as catalysts shows the advantages of wide functional group tolerance, mild reaction conditions, and the use of low-toxic zinc metal. Regarding chiral substances, camphor and its derivatives are not only good chiral auxiliaries in asymmetric synthesis, but also useful chiral scaffolds for asymmetric catalysts. Chiral β-amino alcohol A (DAIB) shows impressive results in catalytic organozinc addition reactions, while β-amino alcohol B is inferior in catalyzing the ethylation reaction (23% ee).

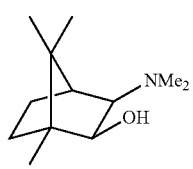

A

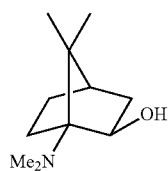

B

SUMMARY OF THE INVENTION

The inventors of the present invention found that the use of less diethylzinc and lower reaction temperatures in the asymmetric addition of diethylzinc to benzaldehyde catalyzed by the known β-amino alcohol B can improve ee (82%). Encouraged by these results, the inventors of the present invention decided to develop a more effective and easily prepared ligand bearing a norbornane structure by enlarging the amino moiety of known (β-amino alcohol B in an asymmetric organozinc addition reaction.

Accordingly, one aspect of the present invention is to provide a camphor-derived β-amino alcohol compound of the following formula (I):

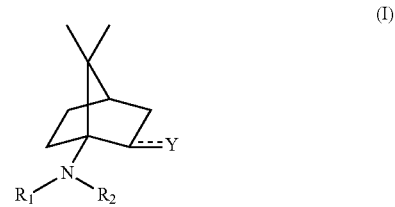

wherein ----- is a single bond or a double bond; Y is OH, when ----- is a single bond; or Y is O, when ----- is a double bond; each of $R_1$ and $R_2$, independently, is alkyl having two or more carbon atoms or $R_1$ and $R_2$ taken together is $(CH_2)_m X (CH_2)_n$; X is O, S, or $CH_2$; and each of m and n, independently, is 1, 2 or 3, and the sum of m and n is 3 or 4.

Regarding the camphor-derived β-amino alcohol compound of the formula (I), preferably, the sum of m and n is 4 when X is O or S.

Regarding the camphor-derived β-amino alcohol compound of the formula (I), preferably, m is 1 or 2 and n is 2.

Regarding the camphor-derived β-amino alcohol compound of the formula (I), preferably, X is O or $CH_2$.

Regarding the camphor-derived β-amino alcohol compound of the formula (I), preferably, each of $R_1$ and $R_2$, independently, is unsubstituted $C_{2-30}$ alkyl, or $R_1$ and $R_2$ taken together is $(CH_2)_m X(CH_2)_n$; more preferably, each of $R_1$ and $R_2$, independently, is unsubstituted $C_{2-10}$ alkyl, or $R_1$ and $R_2$ taken together is $(CH_2)_m X(CH_2)_n$; and most preferably, $R_1$ and $R_2$ taken together may be $(CH_2)_4$, $(CH_2)_5$ or $(CH_2)_2$—O—$(CH_2)_2$.

Another aspect of the present invention is to provide a method for preparing a camphor-derived β-amino alcohol, including the following step:

(a) providing a compound of the following formula (Ia),

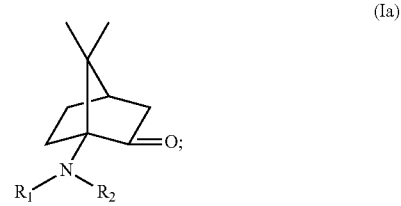

and (b) reducing the compound of the formula (Ia) to form a compound of the following formula (Ib),

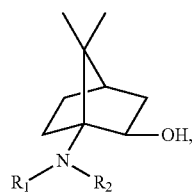
(Ib)

wherein each of $R_1$ and $R_2$ independently is alkyl having two or more carbon atoms, or $R_1$ and $R_2$ taken together is $(CH_2)_mX(CH_2)_n$; X is O, S, or $CH_2$; and each of m and n independently is 1, 2 or 3, and the sum of m and n is 3 or 4.

In the method for preparing a camphor-derived β-amino alcohol according to the present invention, preferably, the compound of the formula (Ia) in the step (a) is provided by reacting a compound of the following formula (1) with $R_6L$ or $L_1(CH_2)_mX(CH_2)_nL_2$,

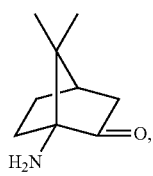
(1)

wherein $R_6$ is alkylene having two or more carbon atoms, and each of L, $L_1$ and $L_2$ independently is a leaving group, for example, halogen (such as F, Cl, Br or I), $-N_2^+$, $-OR_2^+$, $-OSO_2C_4F_9$, $-OSO_2CF_3$, $-OSO_2F$, $-OTs$ (tosylates), $-OMs$ (mesylate), $-OH_2^+$, $-OHR^+$, $-ONO_2$, $-OPO(OH)_2$, $-SR_2^+$, $-NR_3^+$, $-OCOR$ and so on, in which R is $C_{1-10}$ alkyl, such as methyl, ethyl, propyl. Preferably, each of L, $L_1$ and $L_2$ independently is halogen. Additionally, $R_6$ preferably is unsubstituted $C_{2-30}$ alkylene, and more preferably is unsubstituted $C_{2-10}$ alkylene.

In the method for preparing a camphor-derived n-amino alcohol according to the present invention, the compound of the formula (Ia) may be reduced by, for example, $LiBH_4$, $NaBH_4$, $NaBH_4/CeCl_3$ or $NaBH_4/CeCl_3.7H_2O$ (Luche conditions), $LiEt_3BH$, $AlH_3$, DIBAL, $Li(t-BuO)_3AlH$, $Na/NH_3$, $Li/NH_3$, $BH_3$, $B_2H_6$, $BH_3$—$SMe_2$, $BH_3$-pyridine, 9-BBN, $ZnBH_4$, $Li(s-Bu)_3BH$, $Li(s-Bu)_3BH$, $NaBH_4/TiCl_4$ or $LiAla_f$. Preferably, the compound of the formula (Ia) is reduced under Luche condition ($NaBH_4/CeCl_3$ or $NaBH_4/CeCl_3.7H_2O$).

Regarding the compounds of the formulas (Ia) and (Ib), preferably, the sum of m and n is 4 when X is O or S.

Regarding the compounds of the formulas (Ia) and (Ib), preferably, m is 1 or 2 and n is 2.

Regarding the compounds of the formulas (Ia) and (Ib), preferably, X is O or $CH_2$.

Regarding the compounds of the formulas (Ia) and (Ib), preferably, each of $R_1$ and $R_2$, independently, is unsubstituted $C_{2-30}$ alkyl, or $R_1$ and $R_2$ taken together is $(CH_2)_mX(CH_2)_n$; more preferably, each of $R_1$ and $R_2$, independently, is unsubstituted $C_{2-10}$ alkyl, or $R_1$ and $R_2$ taken together is $(CH_2)_mX(CH_2)_n$; and most preferably, $R_1$ and $R_2$ taken together may be $(CH_2)_4$, $(CH_2)_5$ or $(CH_2)_2$—O—$(CH_2)_2$. The camphor-derived β-amino alcohol of the formula (Ib) can be used in asymmetric addition of organozinc to an aldehyde.

Accordingly, yet another aspect of the present invention is to provide a method of asymmetric addition of organozinc to an aldehyde, including a step of reacting $R_3C(O)H$ with $R_4ZnR_5$ in the presence of a catalyst of the following formula (Ib),

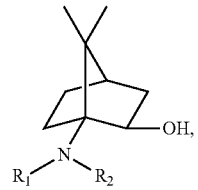
(Ib)

wherein each of $R_1$ and $R_2$, independently, is alkyl having two or more carbon atoms, or $R_1$ and $R_2$ taken together is $(CH_2)_mX(CH_2)_n$; each of $R_3$, $R_4$ and $R_5$, independently, is alkyl, alkenyl, cycloalkyl, cycloalkenyl, heterocycloalkyl, heterocyclialkenyl, aryl, or heteroaryl; X is O, S, or $CH_2$; and each of m and n, independently, is 1, 2 or 3, and the sum of m and n is 3 or 4.

Accordingly, the present invention may prepare a compound represented by the formula of

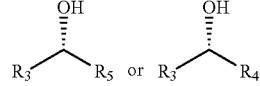

in the majority.

The term "alkyl" refers to a straight or branched hydrocarbon. Examples of alkyl include, but are not limited to, methyl, ethyl, n-propyl, i-propyl, n-butyl, i-butyl, and t-butyl.

The term "alkylene" refers to a straight or branched divalent hydrocarbon. Examples of alkylene include, but are not limited to, methylene ($-CH_2$), ethylene ($-CH_2CH_2-$), and i-propylene ($-CHCH_3CH_2-$).

The term "alkenyl" refers to a straight or branched hydrocarbon containing one or more double bonds. Examples of alkenyl, but are not limited to, include ethenyl, propenyl, allyl, and 1,4-butadienyl.

The term "cycloalkyl" refers to a saturated hydrocarbon ring system. Examples of cycloalkyl include, but are not limited to, cyclopropyl, cyclobutyl, cyclopentyl, cyclohexyl, cycloheptyl, and cyclooctyl.

The term "cycloalkenyl" refers to a non-aromatic hydrocarbon ring system having one or more double bonds. Examples of cycloalkenyl include, but are not limited to, cyclopentenyl, cyclohexenyl, and cycloheptenyl.

The term "heterocycloalkyl" refers to a saturated hydrocarbon ring system having at least one ring heteroatom (e.g., N, O, S or Se). Examples of heterocycloalkyl include, but are not limited to, 4-tetrahydropyranyl.

The term "heterocycloalkenyl" refers to a non-aromatic hydrocarbon ring system having at least one ring heteroatom (e.g., N, O, S or Se) and at least one ring double bond. Examples of heterocycloalkenyl include, but are not limited to, pyranyl.

The term "aryl" refers to an aromatic ring system, which may be a 6-carbon monocyclic, 10-carbon bicyclic, 14-carbon tricyclic aromatic ring system. Examples of aryl groups include, but are not limited to, phenyl, naphthyl, and anthracenyl.

The term "heteroaryl" refers to an aromatic ring system having one or more heteroatoms (such as O, N, S, or Se), which may be a 5 monocyclic, 8-12 membered bicyclic, or 11-14 membered tricyclic aromatic ring system having one or more heteroatoms. Examples of heteroaryl groups include pyridyl, furyl, imidazolyl, benzimidazolyl, pyrimidinyl, thienyl, quinolinyl, indolyl, and thiazolyl.

The above-mentioned alkyl, alkylene, alkenyl, cycloalkyl, cycloalkenyl, heterocycloalkyl, heterocycloalkenyl, aryl and heteroaryl include both substituted and unsubstituted moieties. The term "substituted" refers to one or more substituents (which may be the same or different), each replacing a hydrogen atom. Examples of substituents include, but are not limited to, halogen (such as F, Cl, Br or I), hydroxyl, amino, alkylamino, arylamino, dialkylamino, diarylamino, cyano, nitro, mercapto, carbonyl, carbamido, carbamyl, carboxyl, thioureido, thiocyanato, sulfoamido, alkyl, alkenyl, alkoxy, haloalkyl (i.e. alkyl substituted by one or more halogen atoms), aryl, heteroaryl, cyclyl, heterocyclyl, $CO_2$-alkyl and $CO_2$-alkenyl. Among these above-mentioned substituents, alkyl, alkenyl, alkoxy, aryl, heteroaryl, cyclyl, and heterocyclyl are optionally further substituted with, for example, alkyl, alkenyl, alkoxy, haloalkyl, aryl, heteroaryl, halogen, hydroxyl, amino, mercapto, cyano, nitro, $CO_2$-alkyl or $CO_2$-alkenyl.

Referring $R_3C(O)H$, preferably, $R_3$ is unsubstituted or substituted $C_{1-30}$ alkyl by one or more of halogen, cyano, 5-14 membered heteroaryl, $C_{6-14}$ aryl, $C_{1-30}$ alkoxy, $C_{1-30}$ haloalkyl, $CO_2$—$C_{1-30}$ alkyl and $CO_2$—$C_{2-30}$ alkenyl; $(CH_2)_i R_a$; unsubstituted or substituted $C_{2-30}$ alkenyl by one or more of halogen, cyano, 5-14 membered heteroaryl, $C_{6-14}$ aryl, $C_{1-30}$ alkoxy, $C_{1-30}$ haloalkyl, $CO_2$—$C_{1-30}$ alkyl and $CO_2$—$C_{2-30}$ alkenyl; $(CH_2)_rCH=CH(CH_2)_k R_a$; unsubstituted or substituted $C_{5-14}$ cycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; in which $R_a$ is substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; i is an integer of 1 to 30; and each of r and k independently is an integer of 0 to 30.

Referring $R_3C(O)H$, more preferably, $R_3$ is unsubstituted or substituted $C_{1-10}$ alkyl by one or more of 5-14 membered heteroaryl and $C_{6-14}$ aryl; $(CH_2)_i R_a$; unsubstituted or substituted $C_{2-10}$ alkenyl by one or more of 5-14 membered heteroaryl and $C_{6-14}$ aryl; $(CH_2)_rCH=CH(CH_2)_k R_a$; unsubstituted $C_{5-14}$ cycloalkyl; unsubstituted $C_{5-14}$ cycloalkenyl; unsubstituted or substituted $C_{6-14}$ aryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroaryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; in which $R_a$ is substituted $C_{6-14}$ aryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or substituted 5-14 membered heteroaryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; i is an integer of 1 to 10; and each of r and k independently is an integer of 0 to 10.

Examples of $R_3C(O)H$ include, but are not limited to:

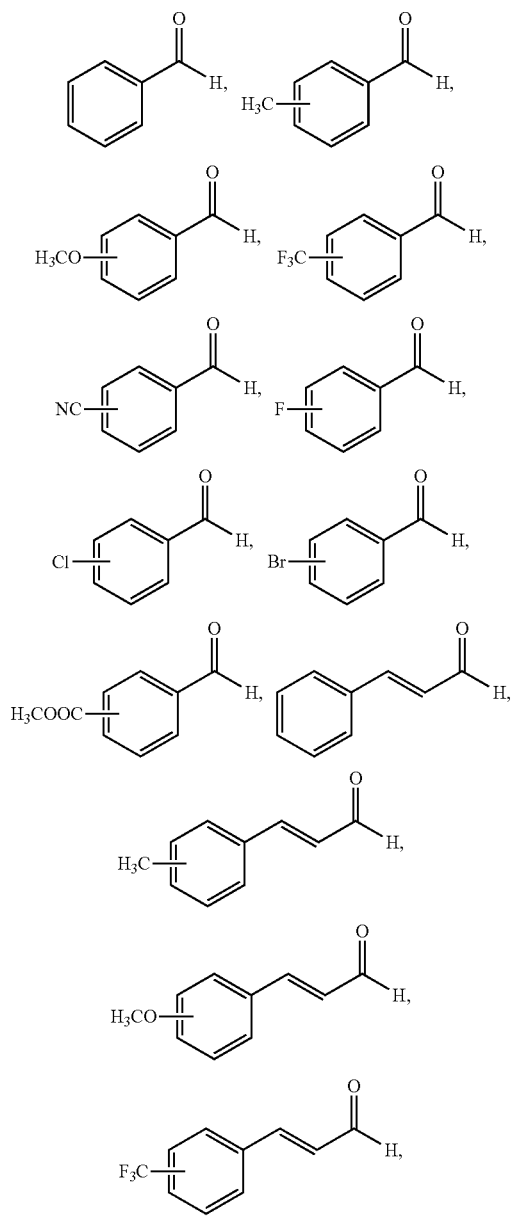

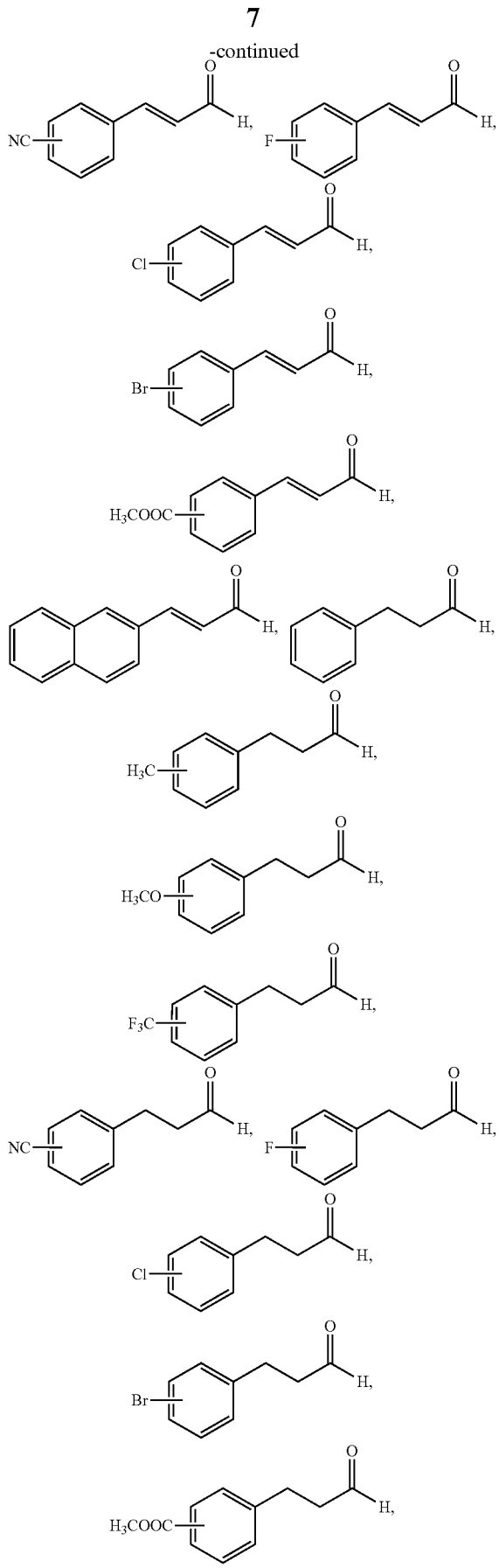
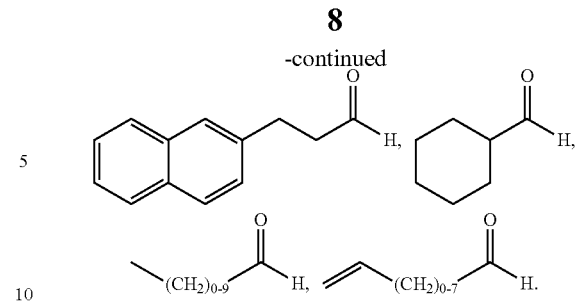

Referring $R_4ZnR_5$, preferably, each of $R_4$ and $R_5$ independently is unsubstituted or substituted $C_{1-30}$ alkyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; unsubstituted or substituted $C_{2-30}$ alkenyl by one or more of halogen, cyano, $C_{1-313}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; unsubstituted or substituted $C_{5-14}$ cycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl.

Referring $R_4ZnR_5$, more preferably, $R_4$ is unsubstituted $C_{1-10}$ alkyl; and $R_5$ is unsubstituted or substituted $C_{1-10}$ alkyl by one or more of $C_{6-14}$ aryl and 5-14 membered heteroaryl; unsubstituted or substituted $C_{2-10}$ alkenyl by one or more of $C_{6-14}$ aryl and 5-14 membered heteroaryl; unsubstituted $C_{5-14}$ cycloalkyl; unsubstituted $C_{5-14}$ cycloalkenyl; unsubstituted or substituted $C_{6-14}$ aryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heteroaryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl.

Examples of $R_4ZnR_5$ include, but are not limited to, $Zn(CH_3)_2$, $Zn(C_2H_5)_2$,

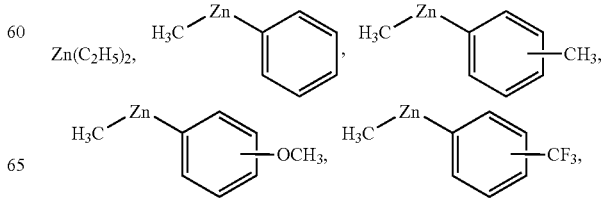

-continued

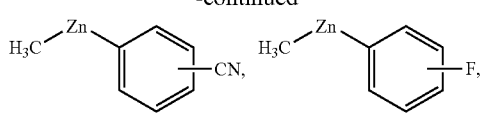

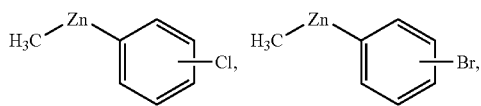

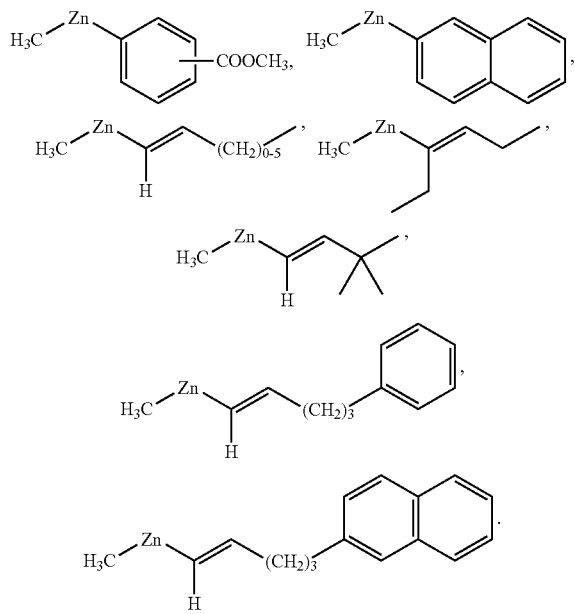

In the method of asymmetric addition of organozinc to an aldehyde according to the present invention, preferably, the compound of the formula (Ib) is used in an amount of 0.01 to 10 mol %, based on the mole of the aldehyde of $R_3C(O)H$.

In the method of asymmetric addition of organozinc to an aldehyde according to the present invention, preferably, the organozinc of $R_4ZnR_5$ is used in an amount of 1 to 2 equivalents, based on the aldehyde of $R_3C(O)H$.

In the method of asymmetric addition of organozinc to an aldehyde according to the present invention, preferably, the reaction between $R_3C(O)H$ and $R_4ZnR_5$ is performed at a temperature in a range of from −10° C. to 40° C.

In the method of asymmetric addition of organozinc to an aldehyde according to the present invention, the reaction between $R_3C(O)H$ and $R_4ZnR_5$ may be performed in a solvent, and preferably in an aprotic solvent, such as hexane, pentane, heptane or a combination thereof.

Accordingly, the present invention provides an effective and easily prepared chiral β-amino alcohol for the catalytic asymmetric addition of diethylzinc to aldehydes. The catalytic system could be applied to both aromatic and aliphatic aldehydes, including linear aliphatic ones, thus generating corresponding secondary alcohols in high yields and enantiomeric excess.

Other objects, advantages, and novel features of the invention will become more apparent from the following detailed description when taken in conjunction with the accompanying drawings.

BRIEF DESCRIPTION OF THE DRAWINGS

None.

DETAILED DESCRIPTION OF THE PREFERRED EMBODIMENT

《Preparation Example》

Synthesis of β-Amino Alcohols 5, 6 and 7

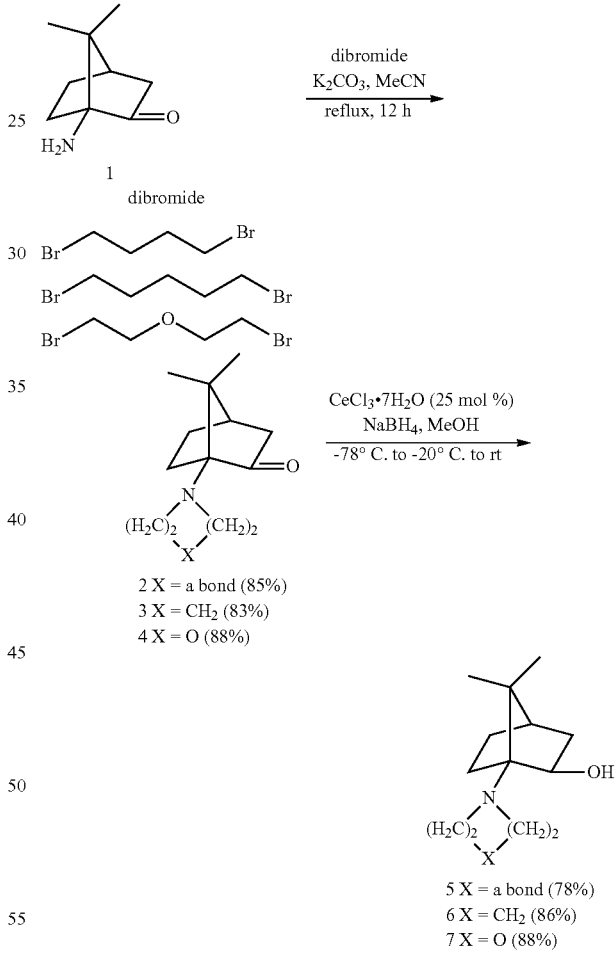

The β-amino alcohol ligands 5-7 were synthesized from the corresponding amino ketone 1 in two steps (Scheme 1). Treatment of amine ketone 1 with 1,4-butane dibromide, 1,5-pentane dibromide, and bis-(2-bromoethyl)ether gave amino ketones 2-4, respectively, in good yields. Finally, the diastereoselective reduction of amino ketones 2-4 with $NaBH_4/CeCl_3 \cdot 7H_2O$ in methanol at −78° C. then slowly to 25° C. yielded the corresponding exo-alcohols 5-7, respectively.

1. General Experimental Procedure for the Synthesis of β-Amino Ketones 2-4

A 10 mL round-bottomed flask containing α-amino ketone 1 (0.10 g, 0.65 mmol) and potassium carbonate (0.20 g, 1.45 mmol) was filled with argon and acetonitrile (2.5 mL) was added. After the mixture was added to the corresponding dibromide (0.70 mmol) and stirred at room temperature for 10 min, the mixture was heated under reflux for 12 h, and the reaction was stopped by the addition of water (5 mL). The mixture was then extracted with $CH_2Cl_2$ (5 mL×3), and the combined organic solution was dried over $Na_2SO_4$ and concentrated to give the crude product, which was purified via column chromatography to yield the desired β-amino ketone.

1.1. (1S)-7,7-Dimethyl-1-pyrrolidin-1-yl-bicyclo[2.2.1]heptan-2-one 2

$[\alpha]_D^{24}$=+45.2 (c 1.0, $CHCl_3$); $^1H$ NMR (400 MHz, $CDCl_3$) δ 3.08-3.03 (m, 2H), 2.85-2.81 (m, 2H), 2.41-2.34 (m, 1H), 2.13 (dt, J=12.8, 3.2 Hz, 1H), 2.05-1.98 (m, 1H), 1.91 (t, J=4.6 Hz, 1H), 1.86-1.67 (m, 6H), 1.40-1.33 (m, 1H), 1.08 (s, 3H), 1.06 (s, 3H); $^{13}C$ NMR (100 MHz, $CDCl_3$) δ 217.4 (C), 77.0 (C), 48.0 ($CH_2$), 46.9 (C), 42.8 (CH), 42.6 ($CH_2$), 27.7 ($CH_2$), 25.9 ($CH_2$), 24.1 ($CH_2$), 22.0 ($CH_3$), 19.7 ($CH_3$); IR (neat) 2963 (s), 2876 (m), 1742 (s) $cm^{-1}$; HRMS calcd for $C_{13}H_{21}NO$ 207.1623. found 207.1620.

1.2. (1S)-7,7-Dimethyl-1-piperidin-1-yl-bicyclo[2.2.1]heptan-2-one 3

$[\alpha]_D^{24}$=+91.4 (c 1.0, $CHCl_3$); mp 78.0-79.0° C.; $^1H$ NMR (400 MHz, $CDCl_3$) δ 2.90-2.82 (m, 2H), 2.78-2.70 (m, 2H), 2.42-2.32 (m, 1H), 2.15 (dt, J=12.6, 3.6 Hz, 1H), 2.00-1.90 (m, 1H), 1.88-1.78 (m, 2H), 1.58-1.46 (m, 5H), 1.45-1.39 (m, 2H), 1.36-1.28 (m, 1H), 1.11 (s, 6H); $^{13}C$ NMR (100 MHz, $CDCl_3$) δ 217.5 (C), 79.2 (C), 49.0 ($CH_2$), 47.4 (C), 43.6 (CH), 43.0 ($CH_2$), 26.8 ($CH_2$), 26.3 ($CH_2$), 25.7 ($CH_2$), 24.5 ($CH_2$), 23.3 ($CH_3$), 21.1 ($CH_3$); IR (neat) 2971 (w), 2926 (m), 1739 (s) $cm^{-1}$; HRMS calcd for $C_{14}H_{23}NO$ 221.1780. found 221.1792.

1.3. (1S)-7,7-Dimethyl-1-morpholin-4-yl-bicyclo[2.2.1]-heptan-2-one 4

$[\alpha]_D^{24}$=+82.5 (c 1.0, $CHCl_3$); mp 89.5-90.5° C.; $^1H$ NMR (400 MHz, $CDCl_3$) δ 3.63 (t, J=4.8 Hz, 4H), 3.00-2.90 (m, 2H), 2.81-2.76 (m, 2H), 2.39-2.33 (m, 1H), 2.08 (dt, J=12.4, 3.6 Hz, 1H), 2.00-1.92 (m, 1H), 1.85-1.80 (m, 2H), 1.57-1.50 (m, 1H), 1.34-1.31 (m, 1H), 1.09 (s, 3H), 1.08 (s, 3H); $^{13}C$ NMR (100 MHz, $CDCl_3$) δ 217.1 (C), 78.6 (C), 67.7 ($CH_2$), 48.5 ($CH_2$), 47.5 (C), 43.8 (CH), 43.1 ($CH_2$), 26.0 ($CH_2$), 25.8 ($CH_2$), 23.3 ($CH_3$), 21.0 ($CH_3$); IR (neat) 2958 (s), 2889 (m), 2850 (s), 1743 (s) $cm^{-1}$; HRMS calcd for $C_{13}H_{21}NO_2$ 223.1572. found 223.1567.

2. General Experimental Procedure for the Synthesis of β-Amino Alcohols 5-7

A 25 mL round-bottomed flask containing the β-amino ketone (0.45 mmol), $CeCl_3 \cdot 7H_2O$ (0.11 mmol), and methanol (3 mL) was cooled to −78° C. Following the addition of $NaBH_4$ (2.11 mmol), the flask was slowly warmed to −20° C. After 2 h at −20° C., the flask was slowly warmed to room temperature, and was kept at ambient temperature for 6 h. The solvents were then removed in vacuo, and to the residue was added water (15 mL) and extracted with $CH_2Cl_2$ (15 mL×3). The organic solution was combined, dried over $Na_2SO_4$, and concentrated to give the crude product, which was purified by column chromatography to yield the pure β-amino alcohol.

2.1. (1S,2R)-7,7-Dimethyl-1-pyrrolidin-1-yl-bicyclo[2.2.1]-heptan-2-ol $[\alpha]_D^{24}$=+1.2 (c 1.0, $CHCl_3$); $^1H$ NMR (400 MHz, $CDCl_3$) δ 3.97 (br, 1H), 3.66 (dd, J=7.8, 3.0 Hz, 1H), 2.67-2.62 (m, 2H), 2.55-2.50 (m, 2H), 1.90-1.85 (m, 1H), 1.81-1.60 (m, 7H), 1.51 (t, J=4.4 Hz, 1H), 1.16-1.06 (m, 1H), 1.10 (s, 3H), 1.03-0.96 (m, 1H), 0.99 (s, 3H); $^{13}C$ NMR (100 MHz, $CDCl_3$) δ 75.1 (CH), 70.1 (C), 47.0 ($CH_2$), 46.3 (C), 45.7 (CH), 38.4 ($CH_2$), 26.1 ($CH_2$), 22.9 ($CH_2$), 22.8 ($CH_3$), 20.7 ($CH_2$), 20.1 ($CH_3$); IR (neat) 3422 (br), 2958 (s), 2877 (s), 2821 (m) $cm^{-1}$; HRMS calcd for $C_{13}H_{23}NO$ 209.1780. found 209.1774.

2.2. (1S,2R)-7,7-Dimethyl-1-piperidin-1-yl-bicyclo[2.2.1]-heptan-2-ol 6

$[\alpha]_D^{24}$=+14.2 (c 1.0, $CHCl_3$); mp 88.5-89.5° C.; $^1H$ NMR (400 MHz, $CDCl_3$) δ 3.72 (d, J=5.2 Hz, 1H), 2.58 (br, 4H), 1.90-1.70 (m, 3H), 1.68-1.36 (m, 8H), 1.18-0.98 (m, 2H), 1.14 (s, 3H), 1.07 (s, 3H); $^{13}C$ NMR (100 MHz, $CDCl_3$) δ 73.6 (CH), 72.8 (C), 48.4 ($CH_2$), 46.7 (CH), 45.9 (C), 37.9 ($CH_2$), 26.7 ($CH_2$), 26.3 ($CH_2$), 24.4 ($CH_2$), 24.0 ($CH_3$), 22.3 ($CH_2$) 20.3 ($CH_3$); IR (neat) 3329 (br), 2958 (s), 2932 (s), 2805 (w) $cm^{-1}$; HRMS calcd for $C_{14}H_{25}NO$ 223.1936. found 223.1945.

2.3. (1S,2R)-7,7-Dimethyl-1-morpholin-4-ylbicyclo[2.2.1]heptan-2-ol 7

$[\alpha]_D^{24}$=+11.0 (c 1.0, $CHCl_3$); mp 35.0-36.0° C.; $^1H$ NMR (400 MHz, $CDCl_3$) δ 3.74-3.66 (m, 5H), 2.67-2.61 (m, 2H), 2.57-2.50 (m, 2H), 1.92-1.76 (m, 3H), 1.69-1.62 (m, 1H), 1.52 (t, J=4.6 Hz, 1H), 1.18-1.00 (m, 2H), 1.14 (s, 3H), 1.06 (s, 3H); $^{13}C$ NMR (100 MHz, $CDCl_3$) δ 72.8 (CH), 71.8 (C), 66.7 ($CH_2$), 47.2 ($CH_2$), 46.0 (CH), 45.3 (C), 37.5 ($CH_2$), 25.7 ($CH_2$), 23.3 ($CH_3$), 21.7 ($CH_2$), 19.8 ($CH_3$); IR (neat) 3415 (br), 2956 (s), 2884 (s), 2850 (m) $cm^{-1}$; HRMS calcd for $C_{13}H_{23}NO_2$ 225.1729. found 225.1713.

《Reaction Example 1》

Asymmetric Diethylzinc Addition with Benzaldehyde Catalyzed by β-Amino Alcohols B and 5-7

The application of 10 mol % of β-amino alcohols B and 5-7 in the asymmetric addition of diethylzinc with benzaldehydes was initially tested at 0° C., and good yields along with excellent ee were obtained (Table 1).

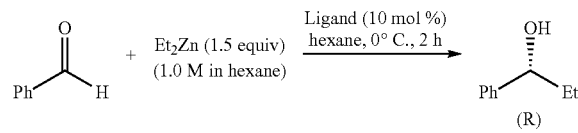

TABLE 1

| Entry | Ligand | Yield$^a$ (%) | ee$^b$ (%) |
|---|---|---|---|
| 1 | B | 91 | 82 |
| 2 | 5 | 89 | 94 |

TABLE 1-continued

| Entry | Ligand | Yield[a] (%) | ee[b] (%) |
|---|---|---|---|
| 3 | 6 | 91 | 95 |
| 4 | 7 | 95 | 95 |

[a]Isolated yield after column chromatography.
[b]Determination by HPLC on the OD-H chiral column.

《Reaction Example 2》

Optimization of the Reaction Conditions with β-Amino Alcohols 7[a]

The addition reaction conditions were optimized with ligand 7, which gave the best yield and ee in the ethylation of benzaldehyde. Various reaction parameters, such as ligand loadings (Table 2, entries 1-3), addition methods (entries 4 and 5), and the amount of diethylzinc (entry 6) were examined. In general, excellent enantioselectivities (94% ee) were observed using 1.5 equiv of diethylzinc in the presence of 5 mol % of β-alcohol 7 at 0° C. The use of less than 1.5 equiv of diethylzinc diminished the enantioinduction (entry 6).

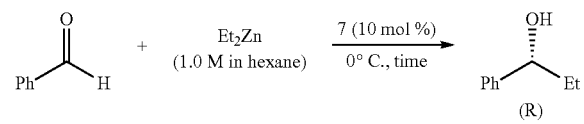

TABLE 2

| Entry | 7 (mol %) | Et$_2$Zn (equiv) | Time (h) | Yield[b] (%) | ee[c] (%) |
|---|---|---|---|---|---|
| 1 | 5 | 1.5 | 6 | 92 | 94 |
| 2 | 2 | 1.5 | 18 | 86 | 84 |
| 3 | 1 | 1.5 | 36 | 75 | 47 |
| 4[d] | 5 | 1.5 | 6 | 90 | 94 |
| 5[e] | 5 | 1.5 | 6 | 92 | 94 |
| 6 | 5 | 1.05 | 6 | 85 | 85 |

[a]The reaction was carried out on a 1.0 mmol scale of benzaldehyde and 1.0 mL of hexane.
[b]Isolated yield after column chromatography.
[c]Determination by HPLC on the OD-H chiral column.
[d]Reverse addition sequence of diethylzinc and benzaldehyde.
[e]Benzaldehyde was slowly added over 10 min.

《Reaction Example 3》

Optimization of Reaction Conditions with β-Amino Alcohol 7 in Different Solvents[a]

The optimization was focused on the solvent effect (see Table 3). Reactions in pentane and heptane were studied at 0° C., and showed excellent ee (entries 1 and 2). When the reaction was conducted in the presence of 5 mol % of β-amino alcohol 7 without solvent it showed no loss of enantioselectivity (entry 3). However, when 2 mol % of ligand was used, the ee value dropped to 78% (entry 4). Interestingly, when the reaction was carried out at ambient temperature, the presence of 2 mol % of ligand led to the corresponding adduct with 93% ee and 90% yield in 15 min (entry 5). There was no improvement in enantioselectivity when diethylzinc in toluene was used, or the reaction was carried out at either 40° C. or −10° C. (entries 6-8). Good enantioselectivity (91% ee) was obtained with 1 mol % of β-amino alcohol 7 at the expense of a longer reaction time (entry 9).

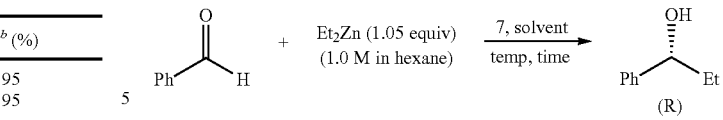

TABLE 3

| Entry | 7 (mol %) | Solvent | Temp (° C.) | Time (h) | Yield[b] (%) | ee[c] (%) |
|---|---|---|---|---|---|---|
| 1 | 5 | pentane (1.0 mL) | 0 | 2 | 92 | 94 |
| 2 | 5 | pentane (1.0 mL) | 0 | 2 | 91 | 94 |
| 3 | 5 | — | 0 | 2 | 86 | 94 |
| 4 | 2 | — | 0 | 6 | 82 | 78 |
| 5 | 2 | — | 25 | 15 min | 90 | 93 |
| 6[d] | 2 | — | 25 | 15 min | 87 | 91 |
| 7 | 2 | — | 40 | 5 min | 85 | 81 |
| 8 | 2 | — | −10 | 1 | 85 | 69 |
| 9 | 1 | — | 25 | 1 | 88 | 91 |
| 10 | 0.5 | — | 25 | 12 | 84 | 18 |

[a]The reaction was carried out on a 1.0 mmol scale of benzaldehyde.
[b]Isolated yield after column chromatography.
[c]Determination by HPLC on the OD-H chiral column.
[d]Et$_2$Zn (1.0M in toluene) was used.

《Reaction Example 4》

Asymmetric Addition of Diethylzinc to Aldehydes Catalyzed by β-Amino Alcohol 7

The reaction conditions in entry 5 showed in Table 3 were utilized to study the application, aldehydes 8a-8k were carefully examined (Table 4). Optically active secondary alcohols with >91% ee were obtained in the cases of aromatic aldehydes (entries 1-6). Alkenyl (entry 7) and aliphatic aldehydes (entries 8-11) were also applicable in the system. It is noteworthy that this methodology could be applied to linear aliphatic aldehydes (entries 10 and 11).

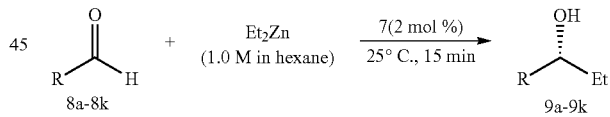

TABLE 4

| Entry | R | Yield[a] (%) | ee[b] (%) |
|---|---|---|---|
| 1 | 3-F—Ph 8a | 95 | 93 |
| 2 | 3-Cl—Ph 8b | 93 | 92 |
| 3 | 2-Me—Ph 8c | 95 | 92 |
| 4 | 3-Me—Ph 8d | 94 | 91 |
| 5 | 3-MeO—Ph 8e | 97 | 94 |
| 6 | 1-Naphthyl 8f | 94 | 91 |
| 7 | (2-Me-cinnamaldehyde) 8g | 96 | 92 |
| 8 | (Hydrocinnamaldehyde) 8h | 89 | 92 |
| 9 | Cyclohexyl 8i | 90 | 93[c] |
| 10 | 10-Decenyl 8j | 90 | 94[d] |
| 11 | Pentyl 8k | 96 | 89[e] |

[a]Isolated yield after column chromatography.
[b]Determination by chiral HPLC.
[c]The ee was determined via its benzoyl ester.
[d]The ee was determined via its p-nitrobenzoyl ester.

1. General Procedure for the Asymmetric Addition of Diethylzinc with Aldehydes 8a-8k Catalyzed by β-amino Alcohol 7

To a 10 mL round-bottomed flask containing ligand 7 (4.5 mg, 0.02 mmol) was added diethylzinc solution (1.05 mmol, 1.0 M in hexane) at room temperature. After being stirred at room temperature for 5 min, the aldehyde (1.0 mmol) was added to the mixture. The reaction was stopped after 15 min by the addition of aqueous $NH_4Cl$ (3 mL, 1 M solution). The mixture was extracted with ether (10 mL×3), and the combined organic solution was dried over $Na_2SO_4$, and concentrated to give the crude product, which was purified by column chromatography to yield the corresponding secondary alcohol. The ee value was determined by HPLC on a chiral stationary phase.

1.1. 1-(3-Fluoro-phenyl)-propan-1-ol 9a

Chiracel AD-H, UV 254 nm, isopropanol/hexanes (1:99), 0.5 mL/min. $t_R$=10.2 min (3.5% for S), 12.7 min (96.5% for R); 93% ee.

1.2. 1-(3-Chloro-phenyl)-propan-1-ol 9b

Chiracel OD-H, UV 254 nm, isopropanol/hexanes (1:99), 0.5 mL/min. $t_R$=38.7 min (4.2% for S), 40.5 min (95.8% for R); 92% ee.

1.3. 1-o-Tolyl-propan-1-ol 9c

Chiracel OB, UV 254 nm, isopropanol/hexanes (1:99), 0.5 mL/min. $t_R$=12.0 min (3.8% for S), 13.5 min (96.2% for R); 92% ee.

1.4. 1-m-Tolyl-propan-1-ol 9d

Chiracel OD-H, UV 254 nm, isopropanol/hexanes (1:99), 0.5 mL/min. $t_R$=9.4 min (95.6% for R), 11.9 min (4.4% for S); 91% ee.

1.5. 1-(3-Methoxy-phenyl)-propan-1-ol 9e

Chiracel OD-H, UV 254 nm, isopropanol/hexanes (2:98), 0.5 mL/min. $t_R$=21.5 min (97.0% for R), 24.0 min (3.0% for S); 94% ee.

1.6. 1-Naphthalen-1-yl-propan-1-ol 9f

Chiracel OD-H, UV 254 nm, isopropanol/hexanes (2:98), 1.0 mL/min. $t_R$=21.7 min (4.3% for S), 42.7 min (95.7% for R); 91% ee.

1.7. 2-Methyl-1-phenyl-pent-1-en-3-ol 9g

Chiracel OD-H, UV 254 nm, isopropanol/hexanes (2:98), 1.0 mL/min. $t_R$=12.6 min (95.9% for R), 14.1 min (4.1% for S); 92% ee.

1.8. 1-Phenyl-pentan-3-ol 9h

Chiracel OD-H, UV 254 nm, isopropanol/hexanes (2:98), 1.0 mL/min. $t_R$=16.5 min (96.2% for R), 27.8 min (3.8% for S); 92% ee.

1.9. Benzoic acid 1-cyclohexyl-propyl ester (benzoyl ester of alcohol 9i)

Chiracel AD-H, UV 254 nm, isopropanol/hexanes (1:99), 0.3 mL/min. $t_R$=14.1 min (96.5% for R), 17.0 min (3.5% for S); 93% ee.

1.10. 4-Nitro-benzoic acid 1-ethyl-undec-10-enyl ester (4-nitrobenzoyl ester of alcohol 9j)

Chiracel OB, UV 254 nm, isopropanol/hexanes (1:400), 0.5 mL/min. $t_R$=25.7 min (2.9% for Se), 30.6 min (97.1% for R); 94% ee.

1.11. 4-Nitro-benzoic acid 1-ethyl-hexyl ester (4-nitro-benzoyl ester of alcohol 9k)

Chiracel OJ, UV 254 nm, isopropanol/hexanes (1:400), 0.5 mL/min. $t_R$=14.3 min (5.6% for S), 16.0 min (94.4% for R); 89% ee.

Although the present invention has been explained in relation to its preferred embodiment, it is to be understood that many other possible modifications and variations can be made without departing from the spirit and scope of the invention as hereinafter claimed.

What is claimed is:

1. A method of asymmetric addition of organozinc to an aldehyde, to form at least one of

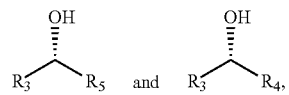

comprising a step of reacting $R_3C(O)H$ with $R_4ZnR_5$ in the presence of a catalyst of the following formula (Ib),

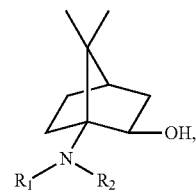

(Ib)

wherein
each of $R_1$ and $R_2$, independently, is alkyl having two or more carbon atoms, or $R_1$ and $R_2$ taken together is $(CH_2)_m X(CH_2)_n$;
each of $R_3$, $R_4$ and $R_5$, independently, is alkyl, alkenyl, cycloalkyl, cycloalkenyl, heterocycloalkyl, heterocycloalkenyl, aryl, or heteroaryl;
X is O, S, or $CH_2$; and
each of m and n, independently, is 1, 2 or 3, and the sum of m and n is 3 or 4.

2. The method as claimed in claim 1, wherein
each of $R_1$ and $R_2$, independently, is unsubstituted $C_{2-30}$ alkyl, or $R_1$ and $R_2$ taken together is $(CH_2)_m X(CH_2)_n$;
$R_3$ is unsubstituted or substituted $C_{1-30}$ alkyl by one or more of halogen, cyano, 5-14 membered heteroaryl, $C_{6-14}$ aryl, $C_{1-30}$ alkoxy, $C_{1-30}$ haloalkyl, $CO_2$—$C_{1-30}$ alkyl and $CO_2$—$C_{2-30}$ alkenyl; $(CH_2)_r R_a$; unsubstituted or substituted $C_{2-30}$ alkenyl by one or more of halogen, cyano, 5-14 membered heteroaryl, $C_{6-14}$ aryl, $C_{1-30}$ alkoxy, $C_{1-30}$ haloalkyl, $CO_2$—$C_{1-30}$ alkyl and $CO_2$—$C_{2-30}$ alkenyl; $(CH_2)_r CH=CH(CH_2)_k R_a$; unsubstituted or substituted $C_{5-14}$ cycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

each of $R_3$ and $R_5$ independently is unsubstituted or substituted $C_{1-30}$ alkyl by one or more of halogen, cyano, $C_{1-30}$ alkoxy, $C_{1-30}$ haloalkyl, $CO_2$—$C_{1-30}$ alkyl, $CO_2$-$C_{2-30}$ alkenyl, $C_{6-14}$ aryl and 5-14 membered heteroaryl; unsubstituted or substituted $C_{2-30}$ alkenyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and $C_{5-14}$ heteroaryl; unsubstituted or substituted $C_{5-14}$ cycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

$R_a$ is substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

i is an integer of 1 to 30; and each of r and k independently is an integer of 0 to 30.

3. The method as claimed in claim 1, wherein each of $R_1$ and $R_2$, independently, is unsubstituted $C_{2-10}$ alkyl, or $R_1$ and $R_2$ taken together is $(CH_2)_m X(CH_2)_n$;

$R_3$ is unsubstituted or substituted $C_{1-10}$ alkyl by one or more of 5-14 membered heteroaryl and $C_{6-14}$ aryl; $(CH_2)_i R_a$; unsubstituted or substituted $C_{2-10}$ alkenyl by one or more of 5-14 membered heteroaryl and $C_{6-14}$ aryl; $(CH_2)_r$ CH=CH$(CH_2)_k R_a$; unsubstituted $C_{5-14}$ cycloalkyl; unsubstituted $C_{5-14}$ cycloalkenyl; unsubstituted or substituted $C_{6-14}$ aryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroaryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl;

$R_4$ is unsubstituted $C_{1-10}$ alkyl;

$R_5$ is unsubstituted or substituted $C_{1-10}$ alkyl by one or more of $C_{6-14}$ aryl and 5-14 membered heteroaryl; unsubstituted or substituted $C_{2-10}$ alkenyl by one or more of $C_{6-14}$ aryl and 5-14 membered heteroaryl; unsubstituted $C_{5-14}$ cycloalkyl; unsubstituted $C_{5-14}$ cycloalkenyl; unsubstituted or substituted $C_{6-14}$ aryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heteroaryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-20}$ alkenyl;

$R_a$ is substituted $C_{6-14}$ aryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or substituted 5-14 membered heteroaryl by one or more of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl;

i is an integer of 1 to 10; and each of r and k independently is an integer of 0 to 10.

4. The method as claimed in claim 1, wherein the sum of m and n is 4 when X is O or S.

5. The method as claimed in claim 4, wherein m is 1 or 2 and n is 2.

6. The method as claimed in claim 1, wherein $R_1$ and $R_2$ taken together is $(CH_2)_4$, $(CH_2)_5$ or $(CH_2)_2 O(CH_2)_2$.

7. The method as claimed in claim 1, wherein the compound of the formula (Ib) is used in an amount of 1 to 10 mol %, based on the mole of the aldehyde of $R_3 C(O)H$.

8. The method as claimed in claim 1, wherein the organozinc of $R_4 ZnR_5$ is used in an amount of 1 to 2 equivalents based on the aldehyde of $R_3 C(O)H$.

9. The method as claimed in claim 1, wherein the reaction between $R_3 C(O)H$ and $R_4 ZnR_5$ is performed at a temperature in a range of from $-10°$ C. to $40°$ C.

* * * * *